(12) United States Patent
Siess et al.

(10) Patent No.: US 7,027,875 B2
(45) Date of Patent: Apr. 11, 2006

(54) INTRAVASCULAR PUMP

(75) Inventors: Thorsten Siess, Wuerselen (DE);
Gerhard Doepper, Wolpertshausen (DE)

(73) Assignee: Impella CardioSystems AG, (DE)

( * ) Notice: Subject to any disclaimer, the term of this patent is extended or adjusted under 35 U.S.C. 154(b) by 206 days.

(21) Appl. No.: 10/432,478

(22) PCT Filed: Nov. 16, 2001

(86) PCT No.: PCT/EP01/13262

§ 371 (c)(1),
(2), (4) Date: May 21, 2003

(87) PCT Pub. No.: WO02/43791

PCT Pub. Date: Jun. 6, 2002

(65) Prior Publication Data

US 2004/0044266 A1    Mar. 4, 2004

(30) Foreign Application Priority Data

Dec. 1, 2000    (DE) ................................ 100 59 714

(51) Int. Cl.
*A61N 1/00* (2006.01)
(52) U.S. Cl. ..................................... 607/116
(58) Field of Classification Search ............... 607/116, 607/119; 604/8, 9, 151, 19
See application file for complete search history.

(56) References Cited

U.S. PATENT DOCUMENTS 5,746,709 A * 5/1998 Rom et al. ..................... 604/8

FOREIGN PATENT DOCUMENTS

| DE | 198 21 307 C1 | 10/1999 |
| EP | 0 629 412 A2 | 12/1994 |
| EP | 0 916 359 A1 | 5/1999 |
| EP | 1 034 808 A1 | 9/2000 |
| WO | WO 97/46270 | 12/1997 |
| WO | WO 99/44651 | 9/1999 |
| WO | WO 00/43053 | 7/2000 |

* cited by examiner

*Primary Examiner*—George Manuel
(74) *Attorney, Agent, or Firm*—Fulwider Patton LLP

(57) ABSTRACT

The pump (10) comprises a drive portion (11) and a pump portion (12) which have such a small diameter that they can be pushed through a blood vessel (31). The pump portion (12) has a flexible cannula (18) connected thereto. In order to reduce the flow resistance of the cannula (18), the cannula (18) can be dilated to a diameter that is larger than that of the drive portion (11) and the pump portion (12), respectively. To be able to introduce the pump into the body by puncturing the blood vessel (31) according to the Seldinger technique, the cannula (18) is set into the constricted state in which it has a small diameter. In the blood vessel (31), it is dilated so that it offers a small flow resistance to the blood to be pumped there.

11 Claims, 8 Drawing Sheets

INTRAVASCULAR PUMP

The invention relates to an intravascular pump with a pump unit comprising a drive portion and a pump portion, and a flexible cannula extending from the pump portion.

An intravascular pump is a pump being adapted to be advanced through the blood vessel system of a patient in order to be introduced, e.g., into the heart. Such an intravascular pump is described in DE 198 21 307 C1. This pump comprises a drive portion with an electric motor and a pump portion driven by the electric motor. To this pump portion, an elongate cannula is connected and placed such that it passes through at least one cardiac valve. At the distal end of the pump, there are openings through which the pump can take in or eject. The pump unit is connected with a catheter including, among other things, the drive lines for the electric motor. The outer diameter of the blood pump is nowhere larger than 8 mm. For this reason, it is possible to advance the pump with the cannula in the vascular system of a human being. It is difficult, however, to introduce the pump into the body. To this end, an operation is typically necessary. It would be desirable to introduce a blood pump into the body by puncturing, by means of the Seldinger technique common with catheters, for example. Therefor, the diameter of the conventional intravascular pumps is too large. It is not possible to reduce the pump cross-section in the region of the cannula because the cannula would be too narrow for the required throughflow of 2 to 2.5 liters per minute. As a result of the high flow resistance of the cannula, a great portion of the pumping power produced by the pump would be lost.

It is the object of the present invention to provide an intravascular pump with a flexible cannula being adapted to be introduced into the body by the technique common with catheters and nevertheless permitting to pump at high flow rates.

This object is solved, according to the invention, with the features indicated in claim 1. Accordingly, the cannula consists of an expandable hose which is able to assume a state with a relatively small first diameter and a state with a relatively large second diameter. According to the invention, the cannula can be constricted such that it can be introduced into the body and the vascular system with the small first diameter. When it is located in the vascular system, it is expanded so that it then takes on the larger diameter required for the pump operation. The cannula is dimensionally stable but elastic. It is introduced into the body in a straight state, but when the pump is advanced into the heart, it preferably takes on a curved configuration corresponding to the radii of the vascular system. The cannula is not substantially compressible in longitudinal direction so that it can be advanced in a blood vessel without being substantially upset.

The applicant has succeeded in reducing the dimensions of the rigid pump unit such that the diameter is not larger than 4.0 mm. Therefore, the pump unit can be introduced into the body like a catheter by puncturing a blood vessel, e.g. a vein. Such a blood pump has an impeller rotating at high rotational speed of at least 30,000 revolutions per minute, typically of 60,000 revolutions per minute. The high pumping capacity associated therewith needs a cannula the outer diameter of which is larger than 4 mm. The pump according to the invention is introduced into the body with a constricted cannula, the cannula subsequently dilating when it is located in the blood vessel. Thus, a small puncturing spot is sufficient. A blood loss and the danger of infection always associated with operations are avoided or reduced. In the expanded state, the diameter of the cannula is larger than that of the drive portion.

The cannula may comprise a material with shape memory. Such a material, e.g., nitinol, forms the frame of a jacket otherwise consisting of plastic and forming the cannula. In its constricted state, the cannula is "frozen" at room temperature, i.e., the nitinol wire is in the plastic range below the transition temperature of glass. If it is heated to body temperature as a result of the body heat, it takes on the expanded state with an enlarged diameter in the superelastic state. Thus, it is possible to expand the outer diameter of the cannula from about 4 mm to about 5.5 mm or more.

The cannula may also consist of an elastic material biased into the expanded state, which is mechanically compressed when being introduced into the body and expands in the interior of the blood vessel.

According to a preferred embodiment of the invention, the cannula is provided with a rigid head piece. The head piece can be used as a dilator. It is provided with an opening for the passage of a guide wire and continuously expands in proximal direction. Such a cannula can be pushed upon a guide wire leading percutaneously into a blood vessel and then acts as a dilator dilating the channel of body tissue containing the guide wire and allows the insertion of the entire pump through the dilated opening.

Hereinafter, embodiments of the invention are explained in detail with respect to the drawings.

Figures 1, 2:
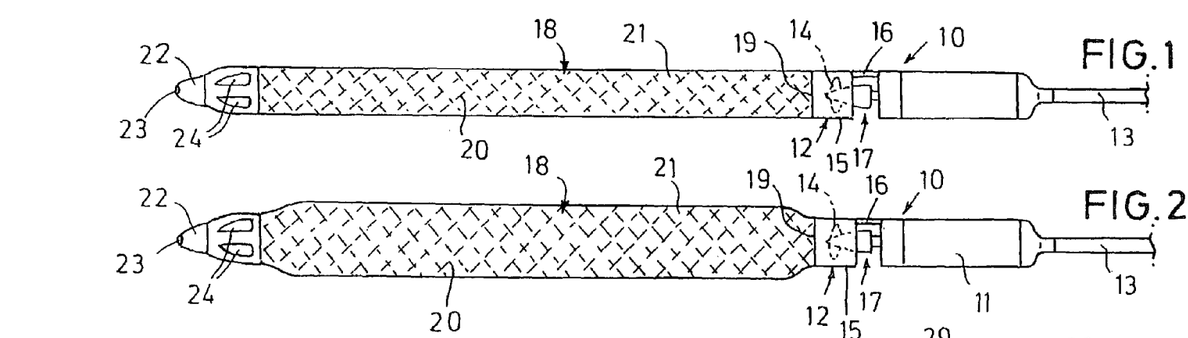
FIG. 1 is a side view of the intravascular pump in the constricted state.
FIG. 2 is a side view of the pump in the expanded state.

The pump illustrated in FIGS. 1 and 2 comprises a pump unit 10 consisting of a drive portion 11 and a pump portion 12. The drive portion 11 has a cylindrical configuration with an outer diameter of about 4 mm. Its proximal end is connected with a catheter 13 which includes a catheter lumen extending throughout and through which the wires for the provision of the electric motor included in the drive portion 11 extend as well. The drive portion 11 drives a shaft on which an impeller 14 located in the pump portion 12 is seated. The impeller 14 rotates in the interior of a ring 15 which forms the pump housing. The pump portion 12 is arranged at an axial distance from the drive portion 11 and connected therewith via longitudinally extending webs 16. The webs 16 bridge the opening 17 forming the outlet or the inlet of the pump, depending on the rotational direction and configuration of the impeller 14. When the opening 17 forms the inlet, the impeller 14 supplies the blood 14 in axial direction into the cannula 18 which is connected to the axial opening 19 forming the outlet. The blood flow can also occur vice versa.

The cannula 18 forms a pump hose having a length of about 50 to 60 mm. It is dimensionally stable but elastic. The cannula 18 includes a supporting structure 20 and a closed jacket 21 covering the supporting structure. At the distal end of the cannula 18, there is a rigid head piece 22 expanding from the distal end to the proximal end and comprising an opening 23 for the passage of a guide wire. There are further openings 24 for the passage of the blood to be pumped at the head piece 22.

In the state illustrated in FIG. 1, the cannula 18 has a small outer diameter which about corresponds to the outer diameter of the pump unit 10, which is 4 mm in the present case. In this state, the cannula 18 is flexible so that it can be bent to be introduced into the vascular system.

In FIG. 2, the pump 10 is illustrated with expanded cannula 18. Now, the outer diameter of the cannula 18 amounts to about 5.4 mm. Compared with FIG. 1, the length of the cannula is unchanged. This state is the operational state of the cannula it takes when the pump unit 10 operates.

Figures 3, 4, 5:
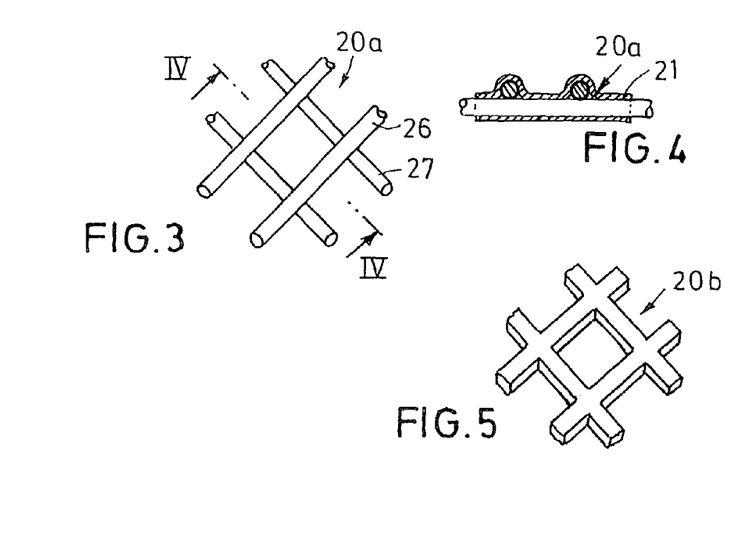
FIG. 3 is an illustration of the wire structure of the deformable cannula.
FIG. 4 is a sectional view along the line IV—IV of FIG. 3, the wires, however, being enclosed by a jacket or a skin.
FIG. 5 shows another embodiment of a lattice of the cannula, the outer jacket, however, not being illustrated.

FIGS. 3 and 4 illustrate an embodiment of the supporting structure 20a of the cannula 18. The supporting structure 20a consists of intersecting elastic wires 26 and 27 forming a parallelogram structure. The wires 26, 27 are wound helically and interconnected by the jacket 21 consisting of plastic. At their intersections, they have such an orientation that the cannula 18 tends to assume the expanded state. On the other hand, the cannula can be brought into the constricted state by compression.

FIG. 5 shows a similar supporting structure 20b consisting of a lattice the bars of which also extend diagonally and form a parallelogram structure. The lattice bars lie in the same plane. The lattice can be made of a tube by laser cutting, for example. It consists of a metal alloy with shape memory, e.g., of nitinol. At room temperature, the lattice is plastically "frozen" in the constricted state and can be superelastically expanded by heating to body temperature.

Figure 6:
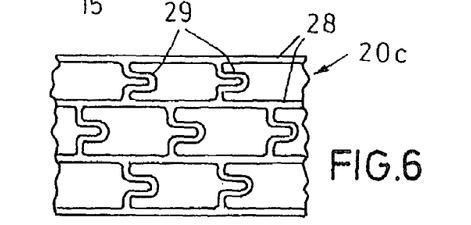
FIG. 6 shows a further embodiment of a supporting structure of the cannula in the constricted state.
Figure 7:
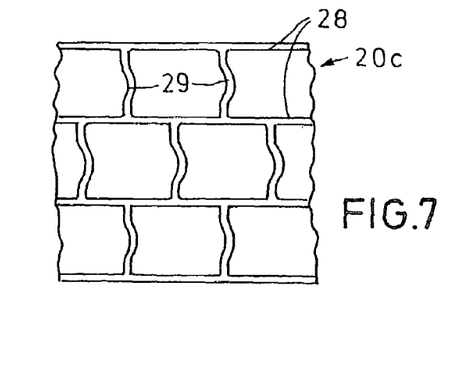
FIG. 7 shows the supporting structure according to FIG. 6 in the expanded state.
Figure 8:
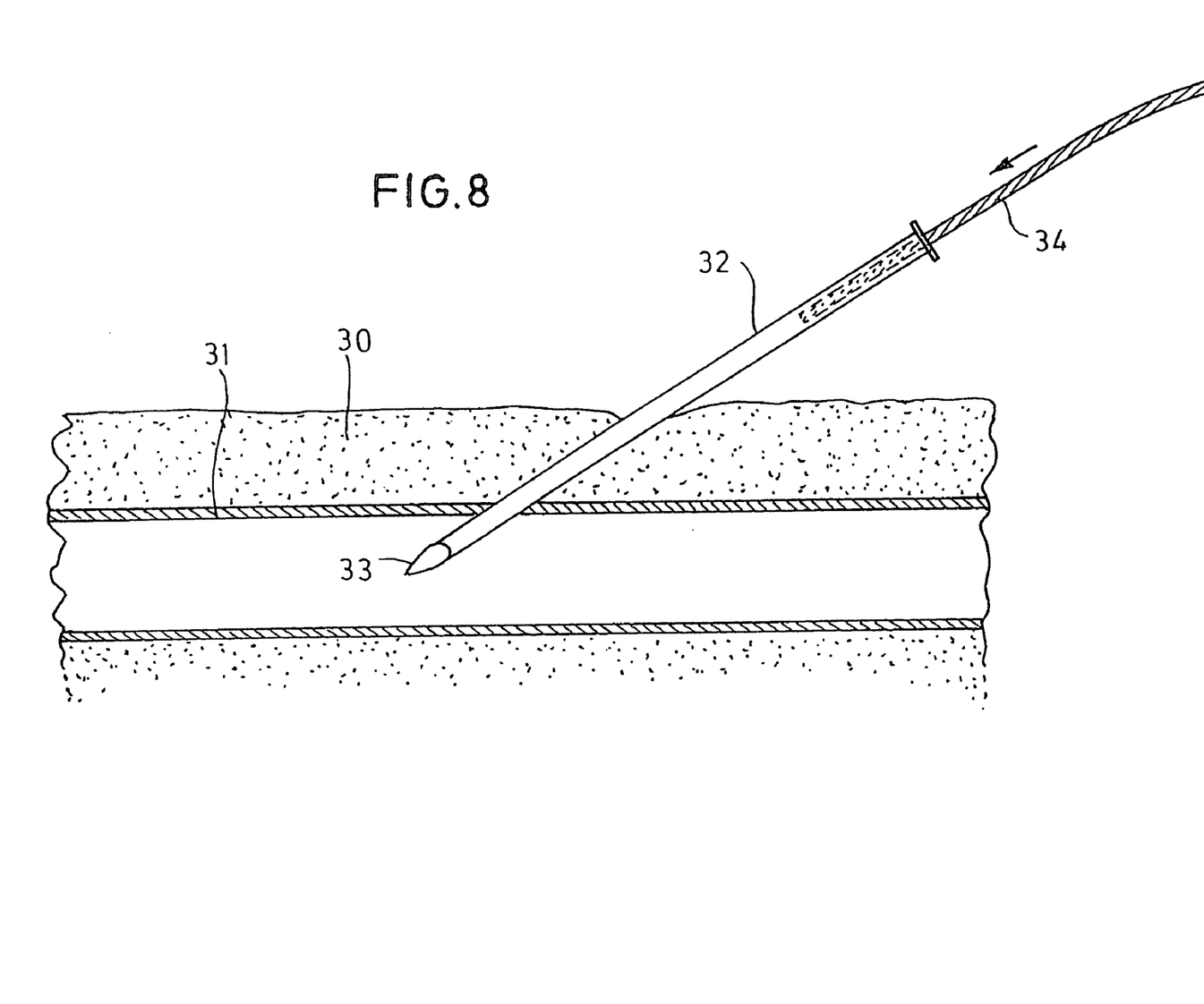
FIG. 8 shows the percutaneous puncturing of a blood vessel and the introduction of a guide wire.

FIGS. 6 and 7 show a further embodiment of a supporting structure 20c with shape memory. This supporting structure includes longitudinally extending straight webs 28 connected by transversely extending loop webs 29. The supporting structure forms a tube. The loop webs 29 have a shape memory. They are frozen in the highly bent state shown in FIG. 6 and can be dilated by heat to the stretched state illustrated in FIG. 7. A jacket consisting of plastic combined with the supporting structure 20c is provided here as well.

As an alternative to a material with shape memory, an elastic spring steel can be used as well which, when formed correspondingly, is only deformed in the elastic range and thus passes to the expanded state after it has been compressed.

Figure 9:
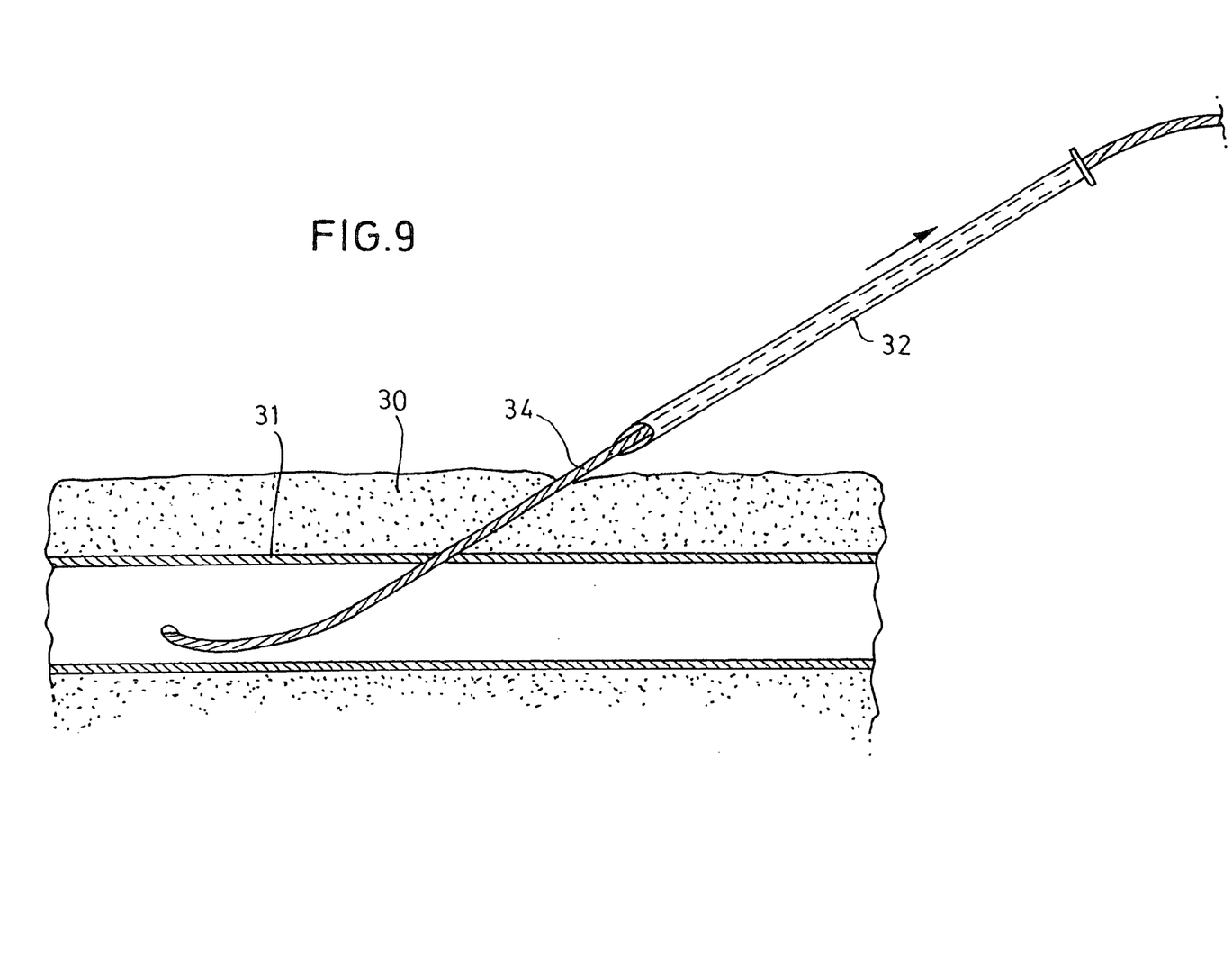
FIG. 9 shows the withdrawal of the steel cannula used for the puncturing.

FIGS. 8 to 12 show a first technique of introducing the pump into the blood vessel system. According to FIG. 8, a blood vessel 31 is first punctured through the skin 30 by means of a steel cannula 32 with a cutting tip 33. Through the steel cannula 32, a guide wire 34 is introduced and then advanced in the blood vessel 31, as is shown in FIG. 9. Thereafter, the steel cannula is withdrawn.

Figure 10:
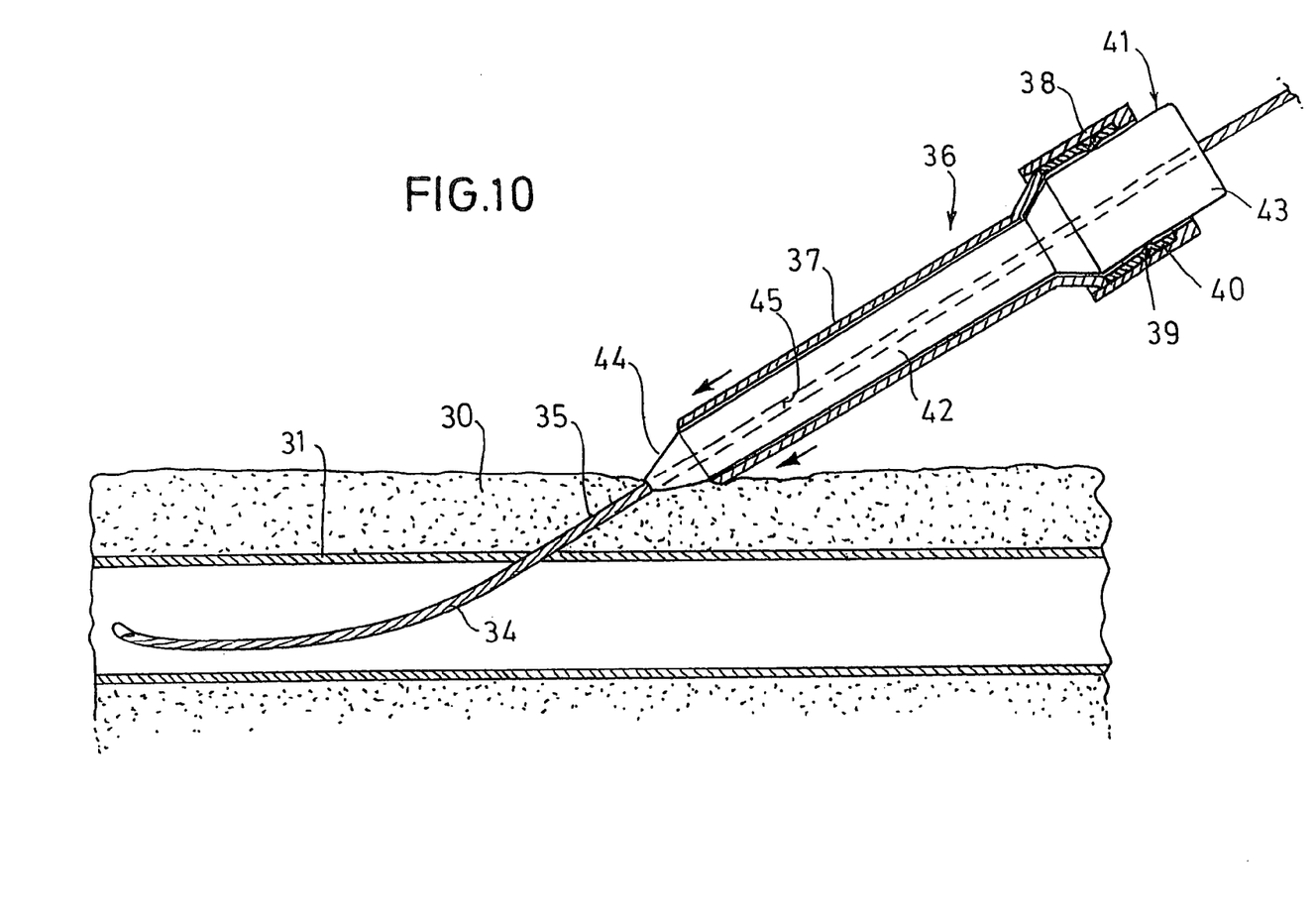
FIG. 10 shows the introduction of a sluice into the blood vessel by using a dilator.

According to FIG. 10, a sluice 36 is introduced into the puncturing channel 35 through which the guide wire 34 passes. The sluice 36 consists of a relatively rigid tube 37 the inner diameter of which is somewhat larger than 4 mm and a hemostatic valve 38 arranged at the proximal end of the tube 37. The hemostatic valve 38 includes an elastomeric annular member 39 which is axially compressed by twisting a screw cap 40 and simultaneously evades radially inward.

In the sluice 36, a dilator 41 is seated which comprises a shank 42 filling up the tube 37 and a head 43 seated in the valve 38 at the rear end. The annular member 39 of the valve is pressed against the head 43 when the screw cap 40 is tensioned so that no blood can escape from the sluice. The dilator 41 comprises a conical tip 44 protruding from the tube 37. A channel 45 through which the guide wire 34 can be pushed extends through the length of the dilator. The dilator 41 serves to dilate the puncturing channel 35 and to introduce the tip of the sluice 36 into the blood vessel 31.

Figure 11:
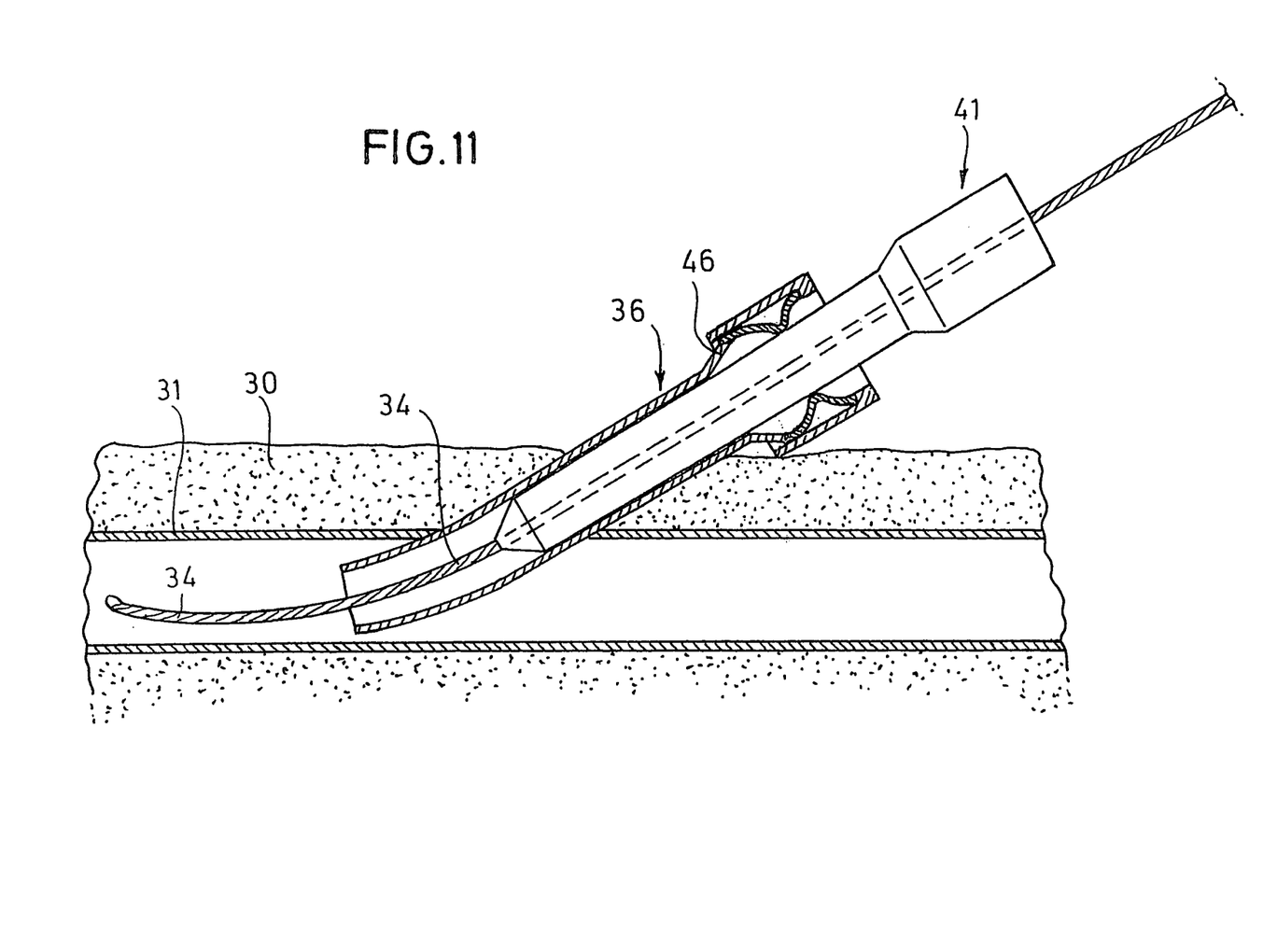
FIG. 11 shows the withdrawal of the dilator.

FIG. 11 shows the withdrawal of the dilator 41 from the sluice 36, so that the latter is now ready for the introduction of the pump 10.

Figure 12:
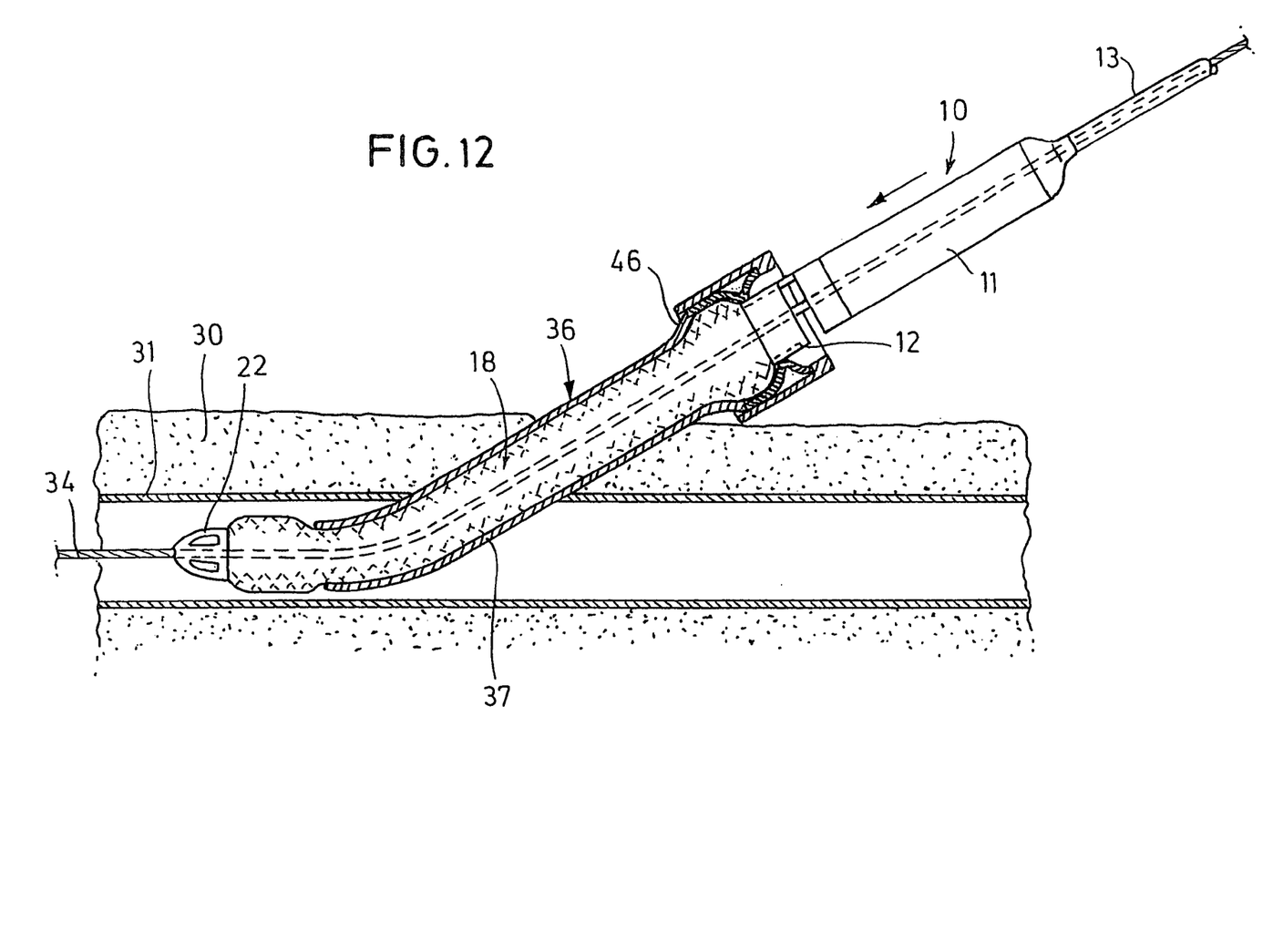
FIG. 12 shows the insertion of the pump through the sluice into the vessel, the cannula of the pump expanding in the interior of the blood vessel.

According to FIG. 12, the pump 10 is introduced into the sluice 36 such that the head 22 is inserted into the proximal end of the sluice first. The head 22 has the same maximum outer diameter as the pump unit 10. Then, the remaining portion of the cannula 18 follows, which is radially compressed by the tapering portion 46 at the rear sluice end and is pushed through the tube 37 in the compressed state. In the blood vessel, the cannula 18 emerges from the sluice 36 and then expands again as a result of its elastic bias. Thus, the entire pump with cannula 18 and pump unit 10 is inserted into the blood vessel over the guide wire 34. Thereafter, the sluice 36 and the guide wire 34 are removed.

Figure 13:
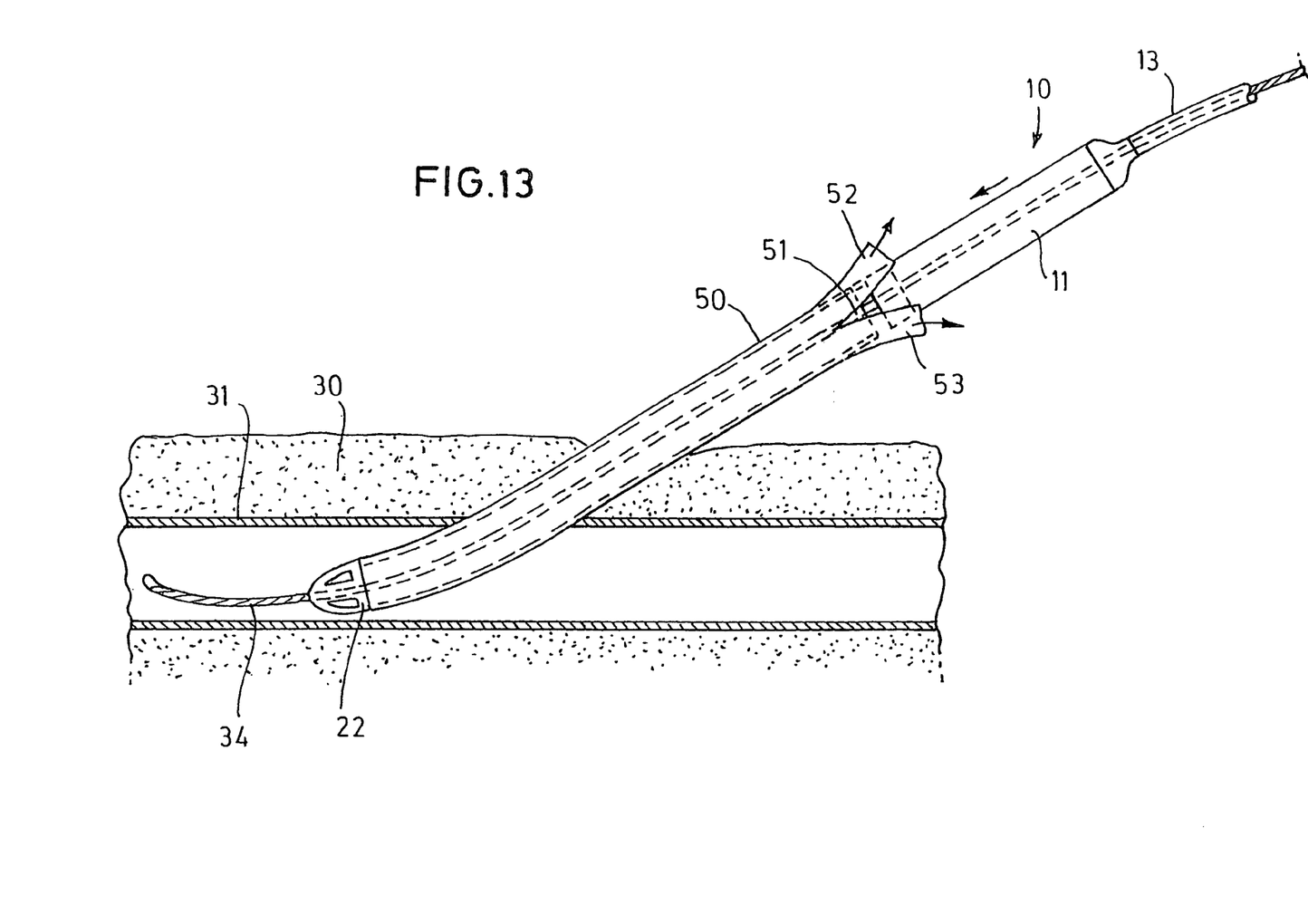
FIG. 13 shows an embodiment in which the cannula is provided with a tearable coating which keeps it in the constricted state and can be peeled off.
Figure 14:
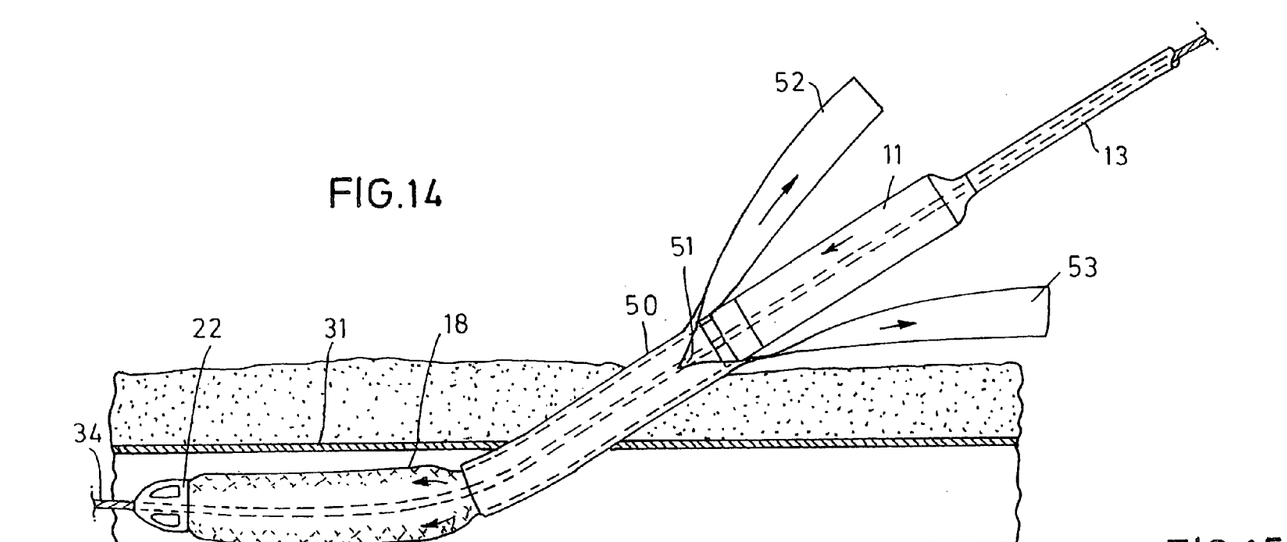
FIG. 14 shows the withdrawal of the coating from the cannula.
Figure 15:
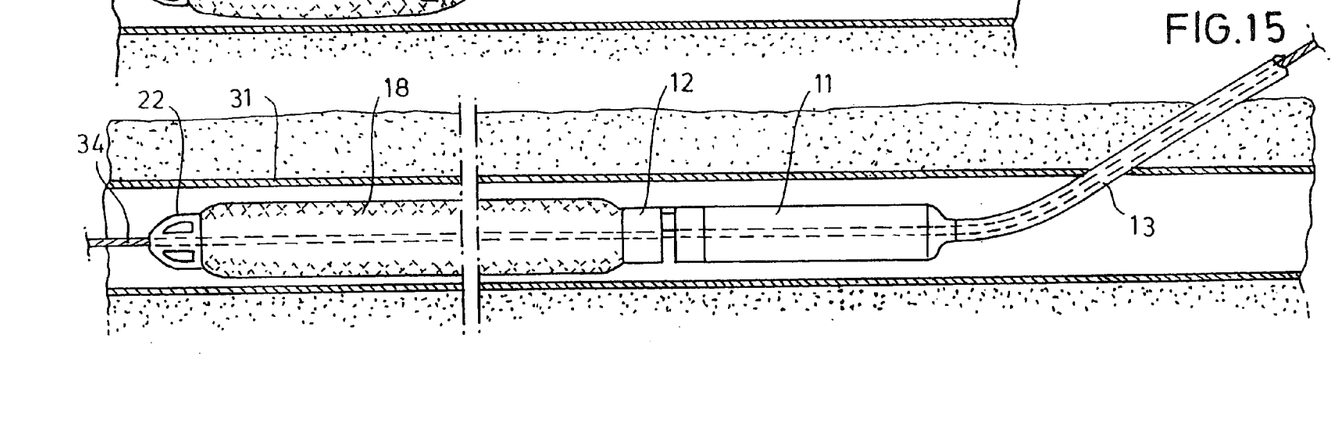
FIG. 15 shows the pump advancing in the blood vessel.

FIGS. 13 to 15 show another manner of introducing the pump 10 into the blood vessel 31. Here, the cannula is held in the constricted state by a tubular coating 50. The coating 50 consists of a thin-walled hose comprising two longitudinally extending fissures 51 at the rear end which allow to rip up the hose into two separate sheets 52, 53. The coating 50 consists of a sheet the molecular structure of which is directed in longitudinal direction of the hose so that each fissure continues in longitudinal direction when the sheets 52, 53 are torn apart.

When the pump is introduced over the guide wire 34, the head 22 serves as dilator dilating the puncturing channel upon advancing the pump 10. Neither a sluice nor a separate dilator is required therefor. When the state illustrated in FIG. 13 is reached, the coating 50 is peeled off in proximal direction, while the pump 10 is further advanced over the guide wire 34. When the coating 50 is withdrawn, it is split. In this manner, the entire pump is introduced into the blood vessel while the coating 50 is withdrawn simultaneously. In the region of the cannula, the outer diameter of the coating 50 amounts to about 3.0 mm, so that, when the hose is withdrawn, the fissures automatically propagate over the pump portion which is approximately 1 mm larger.

Typically, the yield of the pump in the state illustrated in FIG. 15 amounts to 2.0 to 2.5 liters per minute.

If the cannula consists of an elastically dilatable material, i.e., no material with shape memory, it preferably includes a spring steel wire that can be helically wound. By welding individual wires or due to a plastic jacket with varying thickness, the rigidity of the cannula may vary over the cannula length. Preferably, the distal front end of the cannula is soft and the hardness of the cannula increases in rearward direction. The soft cannula tip allows to place the cannula atraumatically in the aortic valve.

What is claimed is:

1. An intravascular pump, comprising:
   a drive portion containing an electric motor;
   a pump portion connected to said drive portion, said pump portion having an axial opening; and
   a cannula projecting distally from said pump portion and being in fluid connection with said axial opening of the pump portion, said cannula comprising an expandable hose adapted to assume a first state with a relatively small diameter and a second state with a relatively large diameter.

2. The pump of claim 1, wherein said cannula is contained in a tubular coating in a constricted state and upon removal of said coating, assumes a dilated state while dilating elastically.

3. The pump of claim 1, wherein said cannula includes a rigid head piece.

4. The pump of claim 1, wherein said drive portion and said pump portion have longitudinally extending channel for a guide wire formed therein.

5. The pump of claim 1, wherein said cannula is radially elastic.

6. The pump of claim 5, wherein said cannula has a rigidity that increases proximally.

7. An intravascular pump, comprising:
   a drive portion;
   a pump portion connected to said drive portion; and
   a cannula projecting from said pump portion comprising an expandable hose adapted to assume a first state with a relatively small diameter and a second state with a relatively large diameter, wherein said cannula comprises a material with shape memory which assumes the first state at a low temperature and assumes the second state at higher temperature.

8. An intravascular pump, comprising:
   a drive portion;
   a pump portion connected to said drive portion; and
   a cannula projecting from said pump portion comprising an expandable hose adapted to assume a first state with a relatively small diameter and a second state with a relatively large diameter, wherein said cannula is contained in a tubular coating in a constricted state and upon removal of said coating, assumes a dilated state while dilating elastically, and wherein said coating includes longitudinally extending fissures to enable said coating to be torn into two separate sheets.

9. The pump of claim 8, wherein said sluice includes a seal that engages said cannula.

10. An intravascular pump, comprising:
    a drive portion;
    a pump portion connected to said drive portion; and
    a cannula projecting from said pump portion comprising an expandable hose adapted to assume a first state with a relatively small diameter and a second state with a relatively large diameter; and
    a tubular sluice through which said cannula is advanceable in its first state.

11. The pump of claim 10, wherein said head piece has an opening formed therein for passage of a guide wire therethrough.

* * * * *